(12) United States Patent
De Ponti

(10) Patent No.: US 6,506,367 B2
(45) Date of Patent: Jan. 14, 2003

(54) ORAL COMPOSITION

(75) Inventor: Rita Cristina De Ponti, Milan (IT)

(73) Assignee: Unilever Home & Personal Care USA, a division of Conopco, Inc., Greenwich, CT (US)

(*) Notice: Subject to any disclaimer, the term of this patent is extended or adjusted under 35 U.S.C. 154(b) by 0 days.

(21) Appl. No.: 09/933,592

(22) Filed: Aug. 21, 2001

(65) Prior Publication Data

US 2002/0048554 A1 Apr. 25, 2002

(30) Foreign Application Priority Data

Aug. 21, 2000 (EP) .............................. 00307120

(51) Int. Cl.⁷ ................................................ A61K 7/16
(52) U.S. Cl. ......................................... 424/49; 424/401
(58) Field of Search .................................... 424/401, 49

(56) References Cited

U.S. PATENT DOCUMENTS 4,098,878 A * 7/1978 Baines et al. ................. 424/49
4,346,072 A * 8/1982 Baines et al. ................. 424/49
4,639,370 A   1/1987 Carli ........................... 424/80

FOREIGN PATENT DOCUMENTS

WO     99/17736     4/1999

OTHER PUBLICATIONS

Partial European Search Report.

* cited by examiner

Primary Examiner—Jose' G. Dees
Assistant Examiner—Konata M. George
(74) Attorney, Agent, or Firm—Milton L. Honig

(57) ABSTRACT

Oral composition comprising a co-ground of at least two ingredients which are co-ground without the use of solvents and wherein the co-ground comprises each of at least two ingredients at a level of at least 5% by weight of the total weight of the co-ground, characterised in that the composition is an aqueous composition.

6 Claims, No Drawings

ORAL COMPOSITION

The present invention relates to an oral composition.

Co-ground products are known in the pharmaceutical field for providing improved solubility to particular agents. Such products have improved dissolution rates when the product is wetted. Typical products are described in EP 0 371 431 (Vectorpharma) where an active substance is mixed with a support substance and co-ground in a mill. The end product is then dried before it can be used.

Co-grounds have also been disclosed for topical cosmetic purposes. WO 99/17736 (Telos) describes how amorphisation results in much a higher solubilisation kinetics profile, in conditions of supersaturation, compared with using the crystalline forms of an active. The co-ground typically comprises a binary system of a carrier, which may or may not be inert, and a cosmetic active material which typically has poor solubility characteristics. The two materials are ground together in the absence of a solvent. The cosmetic actives proposed for co-grinding are solids, or have been rendered solid via absorption, inclusion or microcapsulation. Suitable carriers with which the actives can be co-ground include organic materials such as starches, polyvinyl pyrrolidone, and phospholidpids to name a few, while inorganic examples include, talc, titanium dioxide, zinc oxide, kaolin, zeolites, siO2, silica gel, calcium phosphate, calcium carbonate and the like. This prior art also discloses how the co-grounds can be made by milling, preferably in a high energy mill.

The prior art also discloses in U.S. Pat. No. 4,098,878 (Baines) that co-grinding is one of a number of possible routes by which an abrasive particle for use in toothpaste may be surface-modified with a fatty acid. The abrasive is disclosed to have different reactive properties when modified during the chosen process. Essentially, the surface modification is a means to mask the reactive groups on the abrasive particle and the surface modifying agent is added only in very small amounts, preferably as little as possible, to coat the abrasive particle. In a way it is a form of encapsulation. This patent also states that the modifying agent is added at from 0.1 to 5% by weight of the abrasive particle.

U.S. Pat. No. 4,346,072 (Baines) discloses a similar technology but states that the amount of surface-modifying agent is from 0.1 to 0.5% by weight of the abrasive.

We have surprisingly found that co-grinding technology can be successfully used in oral care formulations which comprise water and where the co-ground comprises at least two ingredients each of which are present at more than 5% by weight of the total co-ground. It is disclosed in the prior art (Telos) that the co-grounds have improved wettability so it is quite surprising that these can be included in hydrous formulations. In fact, a co-ground ingredient can be included in an oral care formulation with surprising stability despite the presence of water as well as surfactants and ionic materials which would typically interfere with the stability of a material. The prior art mainly teaches that powders can be formulated which, when put into contact with a wet surface, have improved solubility/wettability characteristics. The prior art also teaches that co-grinding may be used to apply small amounts of a surface modifying agent to an abrasive particle.

The invention is thus a particularly useful technological advance in oral care as regulatory affairs and consumer sensory perception play an enormous part in the selection of ingredients. For example, there exist many materials, which have a relatively high efficacy but are not used because they taste unacceptably to the consumer. For example, chlorhexidine is an efficacious anti-microbial material, which is hardly ever used in oral care compositions because of its poor taste, which obviously presents an overwhelming consumer negative. On the other hand, there are some materials, which are virtually essential in oral care technology but have a noticeable negative effect on some of the other materials which could provide a consumer benefit. For example, sodium lauryl sulphate (SLS) is a preferred foaming agent in oral care compositions. Unfortunately, SLS has a negative effect on the efficacy of cationic anti-microbial materials such as cetylpyridinium chloride. As such, these materials cannot be used to their fullest in oral care.

Accordingly, we have surprisingly found that the inclusion of co-ground products in oral care formulations can provide an improvement for the consumer, depending upon the ingredients chosen in the co-ground. For example, the use of flavours in a co-ground can provide improved or even prolonged flavour release. Actives which are unstable in the presence of common oral care ingredients such as surfactants can now be used in a co-ground to provide a previously unattainable benefit. This has the further advantage that ingredients which were unstable in the presence of each other but which were stored independently in separate chambers until use may now be formulated in a single tube thus providing a cheaper product. Further, ingredients which were not included in commercially available oral care products before now because of poor sensory perception, e.g. taste or low-foaming, may now be included in a co-ground form which alters the perception profile and provides an improved benefit to the consumer.

A first aspect of the invention thus provides an oral composition comprising a co-ground of at least two ingredients which are co-ground without the use of solvents and wherein the co-ground comprises each of at least two ingredients at a level of at least 5% by weight of the total weight of the co-ground, characterized in that the composition is an aqueous toothpaste composition.

The composition according to the invention is an aqueous composition and comprises from 1 to 80%, preferably from 3 to 50%, more preferably from 5 to 30% by weight water.

By 'co-ground' is meant that at least two materials (a carrier and an active) are ground in a mill without the use of solvents as is described in WO 99/17736 the contents of which are incorporated herein by reference, particularly with respect to the nature and the making of co-grounds. However, for the sake of clarity a co-ground is a ground particle, which comprises at least two ingredients, which have been milled together in the absence of a solvent.

The co-grinding process is carried out in a conventional apparatus, such as a ball mill, a cylinder mill, a rotary mill, a grinding mill or a vibrational mill, for times ranging from a few minutes to some hours, for example from 30 minutes to 8 hours. Preferably, the co-grinding process is carried out in a mill which translates vibrational energy to the materials in the co-ground.

The mill is composed of a cylindrical chamber in stainless steel with a polyurethane covering. Small highly packed grinding media made from a very hard material are placed inside the chamber.

The choice of the size and material of the grinding media depends on the properties of the material to be processed and the desired characteristics of the finished product.

The variation in some operating parameters results in a different energy transfer from the mill to the mixture and thus in different final characteristics of the product.

The vibratory mechanism is made up of a special electric motor linked to two "out of balance" counterweights. This entire group of components, attached directly to the base of the grinding chamber, is suspended by high-tension steel springs in order that energy is directly imparted to the grinding media.

The vibration created by the movement of this system is defined according to two physics-related measures: frequency and amplitude. The particularity lies in the fact that the vibration is of a tri-dimensional type, in that it is characterized by a horizontal as well as a vertical component. The former can be modified by changing the grinding angle i.e. by varying the position of one of the two counterweights.

In this way a different load movement is attained, and in addition the energy transmitted to the grinding media is regulated.

The effect of the co-grinding process in a vibrational mill is determined by a number of parameters which may be adjusted by the skilled person according to the desired objectives. Said parameters include the fill-level of the chamber, in addition to the shape, volume and density of the grinding media.

Another important factor in determining the specific energy used in the co-grinding process is the ratio between the mass of material to be ground and the mass of the grinding media. If the ratio is highly skewed towards the grinding media then the energy will be higher.

The correct duration of the process clearly depends on the chemical and physical characteristics of the materials to be co-ground, as well as on the above-described factors.

Finally, the choice of the weight ratio between the ingredients of the co-ground logically depends on the chemical and physical characteristics of the starting materials, and on the desired final objectives.

The co-ground of the invention comprises at least two materials, which are individually present at more than 5% by weight of the co-ground. This thus allows for the presence of the usual level of impurity often found in such ingredients. Preferably, at least one of the ingredients is present at a level ranging from 10 to 95% by weight of the co-ground, more preferably from 20 to 85%, especially from 30 to 75% and most preferably from 40 to 65% by weight of the co-ground. The co-grounds according to the invention thus form an agglomerate comprising said ingredients and it is this agglomerate which surprisingly does not disintegrate when used in a formulation comprising water.

It is also possible for the co-ground to comprise more than two ingredients not including any impurity. For example, the co-ground may comprise three, four or even five or six different ingredients. It is also possible to prepare one co-ground with two ingredients and then use this product in another co-grinding step to increase the number of ingredients and perhaps change the characteristics of the end result. Where the co-ground comprises more than two ingredients it is also possible for it to be prepared by co-grinding all the ingredients in one step.

Obviously, where more than two ingredients are to be used the third and subsequent ingredient may not necessarily be present at more than 5% by weight of the co-ground.

It is also possible to include an ingredient in the co-ground as well as the remainder of the oral care composition. A suitable example of an embodiment according to the invention would thus comprise an active such as example sodium fluoride in both the co-ground and also in the remainder of the formulation thus providing a burst of fluoride ions during brushing and also a longer, slow-release of fluoride for a period of time after brushing.

Typically the oral composition may comprise from 0.001 to 50% by weight of the co-ground. Preferably the oral composition will comprise from 0.01 to 25% by weight and most preferably from 0.1 to 10% by weight of the co-ground.

The ingredients used in the co-ground may be any which provide a benefit to the composition. These may be flavours, flavour enhancers, antimicrobial actives, abrasives, thickeners, slow-release agents, colors, and such like. The remainder of the oral composition may comprise any of the materials commonly used in oral care formulations whether as active in the co-ground or active in the remainder of the composition. These include:

antimicrobial agents, e.g. Triclosan, chlorhexidine, copper-, zinc- and stannous salts such as zinc citrate, zinc sulphate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds, such as 2,2' methylenebis-(4-chloro-6-bromophenol);

anti-inflammatory agents such as ibuprofen, flurbiprofen, aspirin, indomethacin etc.;

anti-caries agents such as sodium-, calcium-, magnesium- and stannous fluoride, aminefluorides, disodium monofluorophosphate, sodium trimeta phosphate and casein;

plaque buffers such as urea, calcium lactate, calcium glycerophosphate and strontium polyacrylates;

vitamins such as Vitamin C;

plant extracts;

desensitising agents, e.g. potassium citrate, potassium chloride, potassium tartrate, potassium bicarbonate, potassium oxalate, potassium nitrate and strontium salts;

anti-calculus agents, e.g. hypophosphite-containing polymers, organic phosphonates and phosphocitrates etc.;

gum protection agents, e.g. vegetable oils such as sunflower oil, rape seed oil, soybean oil and safflower oil; silicone oil; and hydrocarbon oil. The gum protection agent may be an agent capable of improving the permeability barrier of the gums. A complete description of agents capable of improving the permeability barrier of the gum is found in our co-pending application PCT/EP99/03368;

biomolecules, e.g. bacteriocins, antibodies, enzymes, etc.;

flavours, e.g. peppermint and spearmint oils;

preservatives;

opacifying agents;

coloring agents;

pH-adjusting agents;

sweetening agents;

pharmaceutically acceptable carriers, e.g. starch, sucrose, water or water/alcohol systems etc.;

surfactants, such as anionic, nonionic, cationic and zwitterionic or amphoteric surfactants;

particulate abrasive materials such as silicas, aluminas, calcium carbonates, dicalciumphosphates, calcium pyrophosphates, hydroxyapatites, trimetaphosphates, insoluble hexametaphosphates and so on, including agglomerated particulate abrasive materials;

humectants such as glycerol, sorbitol, propyleneglycol, xylitol, lactitol etc.;

binders and thickeners such as sodium carboxymethyl-cellulose, xanthan gum, gum arabic etc. as well as synthetic polymers such as polyacrylates and carboxyvinyl polymers such as Carbopol®;

buffers and salts; and other optional ingredients that may be included are e.g. bleaching agents such as peroxy compounds e.g. potassium peroxydiphosphate, effervescing systems such as sodium bicarbonate/citric acid systems, color change systems, and so on.

Particularly preferred ingredients in the co-ground include those actives which are unstable in the presence of alkali metal anionic surfactants. Such ingredients include triclosan, cetyl pyridinium chloride, chlorhexidine and other ionic substances.

Ingredients particularly suitable in the present invention include the silicas, hydrophilic or lipophilic polymers, such as crospovidone, pectin, dextran, polyvinylpyrrolidone, cellulose and its derivatives, starches and their derivatives, cyclodextrins, phospholipids, fatty acids, sugars and mixtures thereof. A preferred carrier is abrasive silica.

Further co-ground examples include:

Vitamin C co-ground with abrasive silica to improve the stability of Vitamin C over time. This may also include stannous pyrophosphate to improve the stability of the co-ground. Typical examples include:
50% vitamin C
25% abrasive silica
25 stannous pyrophosphate;
63% vitamin C
33% abrasive silica
4% stannous pyrophosphate
33% vitamin C
67% polyvinylpyrrolidone
20% vitamin C
10% stannous pyrophosphate
40% abrasive silica
30% polyvinylpyrrolidone
20% vitamin C
70% abrasive silica
10% stannous pyrophosphate
50% Vitamin C
9% stannous pyrophosphate
41% abrasive silica
50% Vitamin C
16.7% stannous pyrophsophate
33.3% abrasive silica Glyceryl monooleate (GMO) with abrasive silica to prevent the inhibition of the sensitive teeth effect of GMO by SLS;

Anti-microbial actives with abrasive silica, such as Chlorhexidine, Triclosan, Zinc etc. to improve retention in the oral cavity and also to prevent their interaction with materials in the remainder of the composition;

SLS co-ground with abrasive silica to improve foaming effect of SLS;

Chalk co-ground with abrasive silica to improve the compatibility of chalk with other ingredients.

Particular embodiments of the invention are now illustrated with the following examples:

EXAMPLE 1

A product according to the invention comprising a co-ground of sodium fluoride as active and petroleum jelly as carrier was made according to the methods described in WO99/17736 (Telos). The delivery of fluoride can be prolonged using this co-ground instead of putting the sodium fluoride in the composition in the usual fashion.

| | % w/w | | | | |
|---|---|---|---|---|---|
| Ingredient | 1 | 2 | 3 | 4 | 5 |
| Water | 26.79 | 26.43 | 25.43 | 23.43 | 27.11 |
| Sorbitol | 45 | 45 | 45 | 45 | 45 |
| PEg-32 | 5 | 5 | 5 | 5 | 5 |
| Sodium Saccharin | 0.17 | 0.17 | 0.17 | 0.17 | 0.17 |
| Colour | 1 | 1 | 1 | 1 | 1 |
| Cellulose Gum | 0.9 | 0.9 | 0.9 | 0.9 | 0.9 |
| Sodium Lauryl Sulphate | 1.5 | 1.5 | 1.5 | 1.5 | 1.5 |
| Hydrated Silica | 18 | 18 | 18 | 18 | 18 |
| Aroma | 1 | 1 | 1 | 1 | 1 |
| Sodium Fluoride | | | | | 0.32 |
| Co-ground: Sodium fluoride, petroleum jelly (50:50) | 0.64 | 1 | 2 | 4 | |

For each of the five samples illustrated above the amount of fluoride released over a period of time was analysed.

The following is a standard protocol for measuring fluoride and is well known to a man skilled in the art.

1) Panellists are asked to spill a saliva sample before brushing to get the baseline level;

2) Each panellist brushes the teeth for 40 s with 1.5 g of product;

3) Rinse with 10 ml of demineralised water for 5 s twice;

4) 3–5 ml of saliva spill is collected from each patient after 1,2,3 hours from brushing;

Saliva samples are incubated with TisabIII at 80° C. overnight.

Fluoride is then measured by using a specific electrode after calibration.

The following table shows that the amount of fluoride retained in the oral cavity over a short period (3 hour) was much higher for the co-ground samples (2–5) compared to the non co-ground sample (1) showing that more fluoride was retained after brushing. Accordingly, the co-ground comprising fluoride functions as a slow-release of the fluoride.

TABLE

| Sample | Baseline | 1 h | 2 h | 3 h |
|---|---|---|---|---|
| 1 | 0.058 | 0.378 | 0.228 | 0.166 |
| 2 | 0.051 | 0.371 | 0.294 | 0.198 |
| 3 | 0.059 | 0.349 | 0.231 | 0.175 |
| 4 | 0.065 | 0.421 | 0.319 | 0.209 |
| 5 | 0.052 | 0.445 | 0.262 | 0.175 |

EXAMPLE 2

The invention can be further illustrated with reference to the use of a co-ground to improve the stability of Vitamin C in an oral composition.

Formulations A, B, C and D are identical in every way save the presence in C of 6% by weight of the total composition a co-ground comprising 33% vitamin C, 64% hydrogenated palm oil and the remainder stannous pyrophosphate. D comprises a co-ground of 33% vitamin C and the remainder of abrasive silica. A and B also contain 6% by weight vitamin C in lieu of co-ground vit C.

| Ingredients | A | B | C % W/W | D |
|---|---|---|---|---|
| Aqua | to 100 | to 100 | to 100 | to 100 |
| Sorbitol | 58 | 58 | 58 | 58 |
| Sodium Saccharin | 0.2 | 0.2 | 0.2 | 0.2 |
| Sodium Fluoride | 0.32 | 0.32 | 0.32 | 0.32 |
| CI 77891 | 1 | 1 | 1 | 1 |
| PEG-32 | 2 | 2 | 2 | 2 |
| Stannous Pyrophosphate | 1 | 1 | 1 | 1 |
| Sodium Hydroxide | 0.18 | 0.18 | 0.18 | 0.18 |
| Aqua | 1.5 | 1.5 | 1.5 | 1.5 |
| Cellulose Gum | 0.6 | 0.6 | 0.6 | 0.6 |
| Hydrated Silica | 8 | 8 | 8 | 8 |
| Hydrated Silica | 10 | 10 | 10 | 10 |
| Sodium Lauryl Sulfate | 1.5 | 1.5 | 1.5 | 1.5 |
| Ascorbic Acid | 6 | 6 | 0 | 0 |
| Co-ground vit C (33%), hydrogenated palm oil (63%), stannous pyrophosphate (4%) | 0 | 0 | 6 | 0 |
| Co-ground vit C (33%) and abrasive silica (67%) | 0 | 0 | 0 | 6 |

The stability of vitamin C at 25° C. was measured by standard titration.

| | Amount of Vitamin C remaining (%) | | | |
|---|---|---|---|---|
| Time (months) | A | B | C | D |
| 0 | 100 | 100 | 100 | 100 |
| 1 | 29 | 35 | | |
| 3 | | | 91 | 87 |
| 6 | | | 89 | 82 |

Clearly the presence of Vitamin C in a co-ground prolongs its effectiveness in an oral care composition in that it is significantly more stable in co-ground form.

What is claimed is:

1. Oral toothpaste comprising a co-ground of at least two ingredients which are co-ground without the use of solvents and wherein the co-ground comprises each of at least two ingredients at a level of at least 5% by weight of the total weight of the co-ground, characterised in that the composition is an aqueous toothpaste composition.

2. Oral composition according to claim 1, wherein at least one of the at least two ingredients of the co-ground is an abrasive silica.

3. Oral composition according to claim 1, wherein the composition comprises a surfactant.

4. Oral composition according to claim 1, wherein the co-ground is an agglomerate of the at least two ingredients.

5. Oral composition according to claim 1, wherein the co-ground comprises at least one of the at least two ingredients in an amount ranging from 10 to 95%.

6. Oral composition according to claim 1, wherein at least one of the at least two ingredients is unstable in the presence of surfactant.

* * * * *